(12) United States Patent
Bryant et al.

(10) Patent No.: US 11,583,305 B2
(45) Date of Patent: Feb. 21, 2023

(54) TOOL FOR CUTTING OR CRIMPING CABLE IN A MEDICAL PROCEDURE

(71) Applicant: Cable Fix LLC, Hernando, MS (US)

(72) Inventors: Carey Bryant, Hernando, MS (US);
Mark Brinker, Houston, TX (US);
William Ricci, Richmond Heights, MO (US)

(73) Assignee: CABLE FIX LLC, Hernando, MS (US)

( * ) Notice: Subject to any disclaimer, the term of this patent is extended or adjusted under 35 U.S.C. 154(b) by 0 days.

(21) Appl. No.: 16/872,306

(22) Filed: May 11, 2020

(65) Prior Publication Data
US 2020/0353530 A1 Nov. 12, 2020

Related U.S. Application Data

(63) Continuation-in-part of application No. 62/845,969, filed on May 10, 2019.

(51) Int. Cl.
| | |
|---|---|
| *A61B 17/88* | (2006.01) |
| *A61B 17/29* | (2006.01) |
| A61B 17/32 | (2006.01) |
| A61B 17/82 | (2006.01) |
| B25B 25/00 | (2006.01) |

(52) U.S. Cl.
CPC .......... *A61B 17/29* (2013.01); *A61B 17/8863* (2013.01); *A61B 17/32* (2013.01); *A61B 17/82* (2013.01); *A61B 17/8861* (2013.01); *A61B 17/8869* (2013.01); *B25B 25/00* (2013.01)

(58) Field of Classification Search
CPC ............ A61B 17/8861; A61B 17/8863; A61B 17/8872; A61B 17/8869; A61B 17/88; A61B 17/82; A61B 17/842; A61B 17/0467; A61B 17/1604; A61B 17/1635; B25B 25/00
See application file for complete search history.

(56) References Cited

U.S. PATENT DOCUMENTS

2008/0195145 A1* 8/2008 Bonutti ................ A61B 17/683
606/205

* cited by examiner

*Primary Examiner* — Amy R Sipp
(74) *Attorney, Agent, or Firm* — Kunzler Bean & Adamson (57) ABSTRACT

Disclosed herein is a tool for cutting or crimping a tensioned cable in a medical procedure. The tool comprises a cable forming assembly that is coupled with an inner shaft. The cable forming assembly comprises a cable former. The tool additionally comprises a central channel, which extends through the inner shaft, an outer tube within which the inner shaft is positioned, and the cable forming assembly along an entire length of each one of the inner shaft, the outer tube, and the cable forming assembly. The central channel is configured to receive and support the tensioned cable in-line with the tool. The cable former is actuatable to cut or crimp the tensioned cable when the tensioned cable passes through the central channel. Translational movement of the outer tube along the inner shaft in an engagement direction actuates the cable former to cut or crimp the tensioned cable.

17 Claims, 8 Drawing Sheets

TOOL FOR CUTTING OR CRIMPING CABLE IN A MEDICAL PROCEDURE

CROSS-REFERENCE TO RELATED APPLICATION

This application claims the benefit of U.S. Provisional Patent Application No. 62/845,969, filed May 10, 2019, which is incorporated herein by reference.

FIELD

The present application relates generally to tools for medical procedures, and more particularly to a tool for cutting or crimping a cable used in a medical procedure.

BACKGROUND

Various medical procedures utilize cables or conventional sutures to secure damaged skeletal tissue or soft tissue. Tissues, such as bones or soft-tissues, that have been fragmented, fractured, broken, torn, pulled, stretched, or otherwise damaged need to be set and held in specific orientations in order to properly heal. Cables or conventional sutures may be useful for stabilizing or connecting torn tissue back together or for facilitating holding bone fragments in place. For example, cerclage cables or conventional sutures can be wrapped around or lie adjacent to bone for fracture reduction, fracture fixation, and crack propagation prevention.

Conventional tools and procedures for cutting or crimping cables or conventional sutures in medical surgeries are generally time-consuming, complex, and usually involve multiple in-situ steps that are difficult to perform. Moreover, such conventional tools require lateral access to the cable, which can be difficult and may require an enlargement of an incision of the body. Additionally, conventional tools that cut or crimp cables do not allow for flush cutting or crimping of the cable relative to a washer, or other component, used to secure the cable to tissue.

SUMMARY

The subject matter of the present application has been developed in response to the present state of the art, and in particular, in response to the problems and needs of conventional tools for cutting or crimping a cable used in a medical procedure. In view of the foregoing, the subject matter of the present application has been developed to provide a tool for cutting or crimping a cable used in a medical procedure that overcomes many, if not all, of the shortcomings of the prior art.

Disclosed herein is a tool for cutting or crimping a tensioned cable in a medical procedure. The tool comprises an inner shaft. The tool also comprises an outer tube within which the inner shaft is positioned. The outer tube is concentric with the inner shaft and translationally movable along the inner shaft. The tool further comprises a cable forming assembly, coupled with the inner shaft such that the cable forming assembly is co-movable with the inner shaft and the outer tube is translationally movable along the cable forming assembly. The cable forming assembly comprises a cable former. The tool additionally comprises a central channel, which extends through the inner shaft, the outer tube, and the cable forming assembly along an entire length of each one of the inner shaft, the outer tube, and the cable forming assembly. The central channel is configured to receive and support the tensioned cable in-line with the tool.

The cable former is actuatable to cut or crimp the tensioned cable when the tensioned cable passes through the central channel. Translational movement of the outer tube along the inner shaft in an engagement direction actuates the cable former to cut or crimp the tensioned cable. The preceding subject matter of this paragraph characterizes example 1 of the present disclosure.

The tool further comprises a handle coupled to the inner shaft and the outer shaft. The handle is manually operable to translationally move the outer shaft along the inner shaft in the engagement direction. The preceding subject matter of this paragraph characterizes example 2 of the present disclosure, wherein example 2 also includes the subject matter according to example 1, above.

The handle comprises a back handle portion, non-movably fixed to the inner shaft. The handle further comprises a front handle portion movably coupled to the outer tube. Manual movement of the front handle portion towards the back handle portion urges the outer shaft to translationally move along the inner shaft in the engagement direction. The preceding subject matter of this paragraph characterizes example 3 of the present disclosure, wherein example 3 also includes the subject matter according to any one of examples 1-2, above.

The cable former comprises a cable-forming element, movable in a direction angled relative to the engagement direction, and a lever, pivotable relative to the outer tube and positioned to engage the outer tube as the outer tube translationally moves along the inner shaft in the engagement direction. Engagement between the outer tube and the lever causes the lever to pivot relative to the outer tube and move the cable-forming element in the direction angled relative to the engagement direction to cut or crimp the tensioned cable when the tensioned cable passes through the central channel. The preceding subject matter of this paragraph characterizes example 4 of the present disclosure, wherein example 4 also includes the subject matter according to any one of examples 1-3, above.

The lever comprises an angled surface, which is angled relative to the engagement direction. Engagement between the outer tube and the cable-forming element comprises the outer tube sliding along the angled surface. The preceding subject matter of this paragraph characterizes example 5 of the present disclosure, wherein example 5 also includes the subject matter according to example 4, above.

The cable-forming element comprises a cutting insert, which comprises a through-aperture that defines a portion of the central channel. At least a portion of the through-aperture of the cutting insert comprises a blade. The blade is configured to cut the tensioned cable, when the tensioned cable passes through the through-aperture of the cutting insert and when the cutting insert is moved in the direction angled relative to the engagement direction. The preceding subject matter of this paragraph characterizes example 6 of the present disclosure, wherein example 6 also includes the subject matter according to any one of examples 4-5, above.

The cable-former further comprises a mating insert, which comprises a through-aperture that defines a portion of the central channel. The mating insert further comprises a receptacle, which has a contoured shape. The cutting insert is interposed between the mating insert and the outer tube. The preceding subject matter of this paragraph characterizes example 7 of the present disclosure, wherein example 7 also includes the subject matter according to example 6, above.

The mating insert abuts the cutting insert such that the cutting insert is slidable against the mating insert as the cutting insert moves in the direction angled relative to the engagement direction. The preceding subject matter of this paragraph characterizes example 8 of the present disclosure, wherein example 8 also includes the subject matter according to example 7, above.

The direction angled relative to the engagement direction is a direction perpendicular to the engagement direction. The preceding subject matter of this paragraph characterizes example 9 of the present disclosure, wherein example 9 also includes the subject matter according to any one of examples 4-8, above.

The cable former comprises a crimping die positioned to engage the outer tube as the outer tube translationally moves along the inner shaft in the engagement direction. Engagement between the outer tube and the crimping die causes the crimping die to move in the direction angled relative to the engagement direction to crimp the tensioned cable when the tensioned cable passes through the central channel. The preceding subject matter of this paragraph characterizes example 10 of the present disclosure, wherein example 10 also includes the subject matter according to any one of examples 1-5, above.

The crimping die comprises a lever, which is pivotable relative to the outer tube and positioned to engage the outer tube as the outer tube translationally moves along the inner shaft in the engagement direction. Engagement between the outer tube and the lever causes the lever to pivot relative to the outer tube and move the crimping die in the direction angled relative to the engagement direction to crimp the tensioned cable when the tensioned cable passes through the central channel. The preceding subject matter of this paragraph characterizes example 11 of the present disclosure, wherein example 11 also includes the subject matter according to example 10, above.

The lever comprises an angled surface, which is angled relative to the engagement direction. Engagement between the outer tube and the cable-forming element comprises the outer tube sliding along the angled surface. The preceding subject matter of this paragraph characterizes example 12 of the present disclosure, wherein example 12 also includes the subject matter according to example 11, above.

The crimping die and the lever form a one-piece monolithic unit. The preceding subject matter of this paragraph characterizes example 13 of the present disclosure, wherein example 13 also includes the subject matter according to example 12, above.

The cable former further comprises a second crimping die, which opposes and is spaced apart from the crimping die. The second crimping die is positioned to engage the outer tube as the outer tube translationally moves along the inner shaft in the engagement direction. Engagement between the outer tube and the second crimping die causes the second crimping die to move in a second direction, angled relative to the engagement direction and toward the crimping die, to crimp the tensioned cable between the crimping die and the second crimping die when the tensioned cable passes through the central channel. The preceding subject matter of this paragraph characterizes example 14 of the present disclosure, wherein example 14 also includes the subject matter according to any one of examples 10-13, above.

The cable former further comprises a base shaft positioned within the outer tube and concentric with the inner shaft. The base shaft comprises a proximal end coupled directly to the inner shaft such that the base shaft is co-movably fixed to the inner shaft. The base shaft comprises a distal end, which is opposite the proximal end and coupled to the cable former. The outer tube is translationally movable along the base shaft. The preceding subject matter of this paragraph characterizes example 15 of the present disclosure, wherein example 15 also includes the subject matter according to any one of examples 1-14, above.

The distal end of the base shaft is selectively releasably coupled to the inner shaft. The preceding subject matter of this paragraph characterizes example 16 of the present disclosure, wherein example 16 also includes the subject matter according to example 15, above.

The tool further comprises a plurality of cable forming assemblies. Each one of the plurality of cable forming assemblies is selectively interchangeably coupleable with the distal end of the base shaft. Each one of the plurality of cable forming assemblies is configured differently than any other one of the plurality of cable forming assemblies. The preceding subject matter of this paragraph characterizes example 17 of the present disclosure, wherein example 17 also includes the subject matter according to example 16, above.

The cable former of at least one of the plurality of cable forming assemblies cuts the tensioned cable when actuated by the outer tube. The cable former of at least one of the plurality of cable forming assemblies crimps the tensioned cable when actuated by the outer tube. The preceding subject matter of this paragraph characterizes example 18 of the present disclosure, wherein example 18 also includes the subject matter according to example 17, above.

Further disclosed herein is a system for cutting a tensioned cable in a medical procedure. The system comprises a tensionable cable. The system also comprises a washer, configured to retain the tensionable cable. The system further comprises a tool. The tool comprises an inner shaft. The tool also comprises an outer tube within which the inner shaft is positioned. The outer tube is concentric with the inner shaft and translationally movable along the inner shaft. The tool further comprises a cable forming assembly, coupled with the inner shaft such that the cable forming assembly is co-movable with the inner shaft and the outer tube is translationally movable along the cable forming assembly. The cable forming assembly comprises a cable former. The tool additionally comprises a central channel, which extends through the inner shaft, the outer tube, and the cable forming assembly along an entire length of each one of the inner shaft, the outer tube, and the cable forming assembly. The central channel is configured to receive and support the tensioned cable in-line with the tool. The cable former comprises a cutting insert, which is movable in a direction angled relative to the engagement direction and comprises a through-aperture that defines a portion of the central channel and at least a portion of the through-aperture of the cutting insert comprises a blade. The blade is configured to cut the tensioned cable, when the tensioned cable passes through the through-aperture of the cutting insert and when the cutting insert is moved in the direction angled relative to the engagement direction. The cable former also comprises a mating insert, which comprises a through-aperture that defines a portion of the central channel. Translational movement of the outer tube along the inner shaft in an engagement direction moves the cutting insert to cut the tensioned cable when passed through the through-aperture of the cutting insert. The mating insert further comprises a receptacle, which has a contoured shape that complements a shape of the washer such that the washer is seatably engaged with the receptacle when the cutting insert cuts the tensioned cable. The cutting insert is interposed between the mating insert and the outer tube. The preceding subject matter of this paragraph characterizes example 19 of the present disclosure.

Additionally disclosed here is a method of cutting or crimping a tensioned cable in a medical procedure. The method comprises passing a tensioned cable through a central channel of a tool such that the cable is in-line with the tool. The method also comprises manually operating a handle of the tool to translationally move an outer tube of the tool relative to an inner shaft of the tool. The method further comprises engaging a cable forming assembly of the tool with the outer tube of the tool as the outer tube translationally moves relative to the inner tube. The method additionally comprises actuating a cable former of the cable forming assembly as the outer tube of the tool engages the cable forming assembly of the tool to cut or crimp the tensioned cable passed through the central channel of the tool. The preceding subject matter of this paragraph characterizes example 20 of the present disclosure.

The described features, structures, advantages, and/or characteristics of the subject matter of the present disclosure may be combined in any suitable manner in one or more examples and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example or implementation. In other instances, additional features and advantages may be recognized in certain examples and/or implementations that may not be present in all examples or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended numbered paragraphs, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings, which are not necessarily drawn to scale, depict only certain examples of the subject matter and are not therefore to be considered to be limiting of its scope, the subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Figure 8:
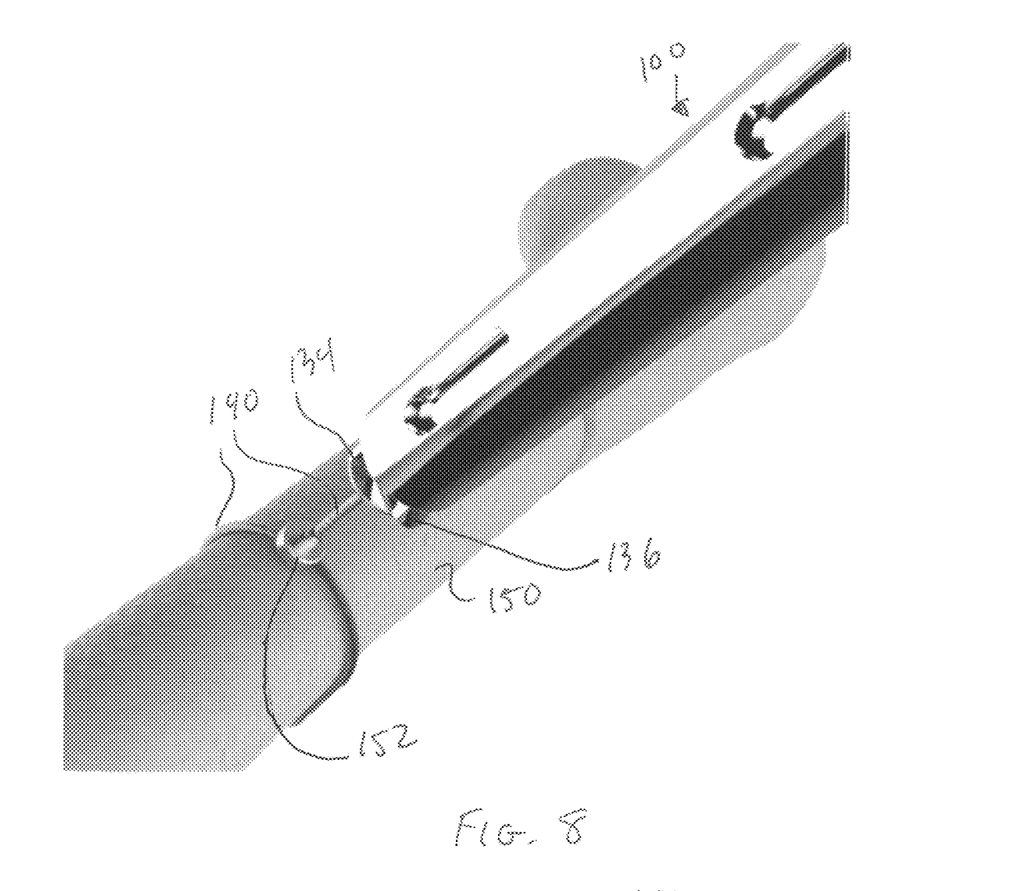
FIG. 8 is a schematic perspective view of a system that includes a tool, a tensionable cable, and a washer, according to one or more examples of the present disclosure.
Figure 9:
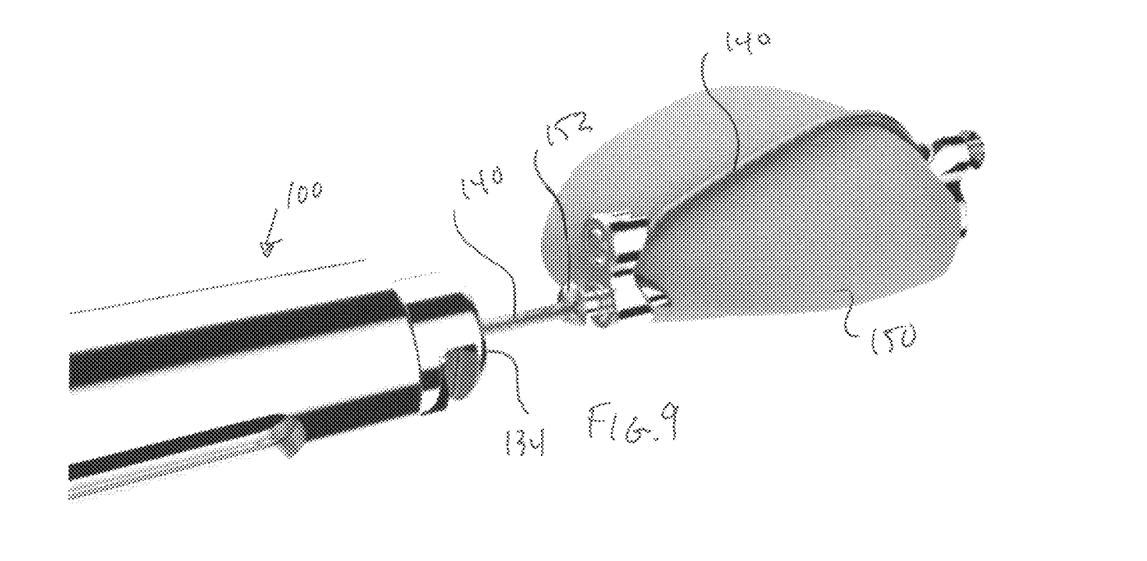
FIG. 9 is a schematic perspective view of a system that includes a tool, a tensionable cable, and a washer, according to one or more examples of the present disclosure.
Figure 10:
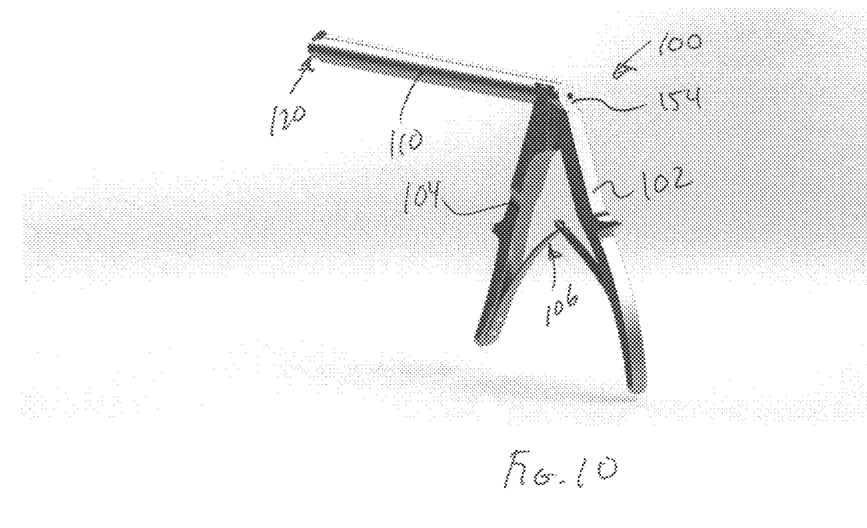
FIG. 10 is a schematic perspective view of a tool, according to one or more examples of the present disclosure.
Figure 11:
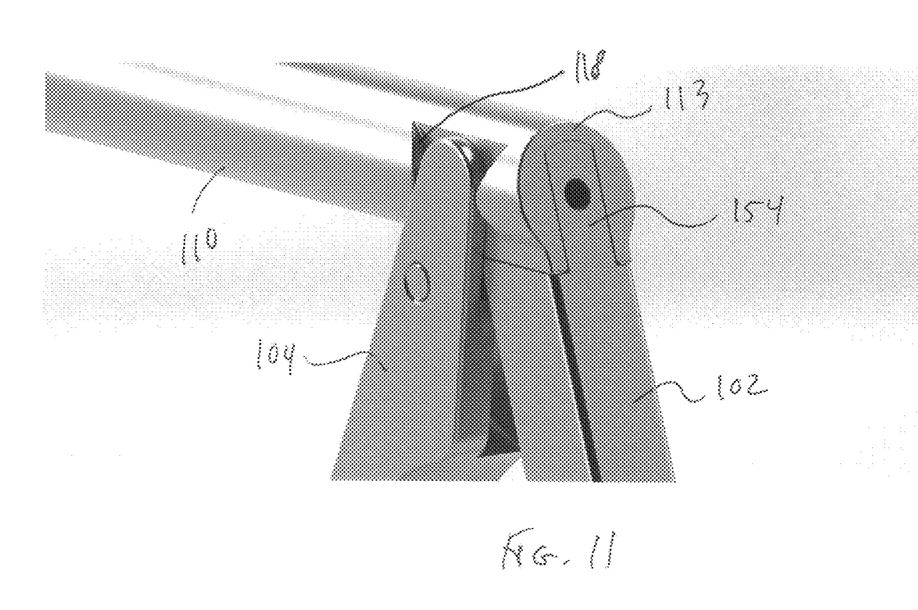
FIG. 11 is a schematic perspective view of a portion of the tool of FIG. 10, according to one or more examples of the present disclosure.

Referring to FIGS. 8 and 9, in some examples, cables 140 are used to suture torn tissue back together and/or to hold bone fragments securely in place. For example, one end of a cable 140 may be anchored to a bone 150, while the other end of the cable 140 is wrapped around the bone to provide external reinforcement after the fractured bone has been set (e.g., a cerclage configuration). In another example, a cable 140 may be used to couple the bone to a soft-tissue segment or to another bone. Often, a washer 152, or other component that facilitates secure coupling of a cable to tissue. In some examples, the washer 152 is part of a crimping system designed to crimp the cable 140 for securing the cable relative to tissue. In other examples, the washer 152 simply facilitates routing and retainment of a cable relative to bone and crimping of the cable is performed independently of the washer 152. After crimping or securing of the cable 140, the cable 140 is cut to remove excess portions of the cable 140.

Generally, the cable 140 is tensioned before being crimped and cut or is in tension when crimped and cut. As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 140 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 140 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension.

Because the cable 140 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 140 to be tensioned to a measurable and adjustable tension improves the reliability and reproducibility of surgical procedures when compared with other medical procedures that do not utilize cables. The cable 140 may be made from any one of various materials. For example, in specific implementations, the cable 140 is made from metal, such as stainless steel, titanium, or other metal.

Described herein are several examples of a tool 100 configured to either cut or crimp a tensioned cable, such as the cable 140. The tool 100 receives the cable 140 in-line with the tool 100. In other words, as the cable 140 is cut or crimped by the tool 100, the cable 140 is coaxial with or extends through the tool 100. Such an in-line arrangement allows the tool 100 to access the cable 140, for cutting or crimping, from above the incision site, rather than from a side of the incision site. Additionally, the tool 100 utilizes a guillotine-like action to cut or crimp the cable 140. Furthermore, because the cable 140 is in-line with the tool 100, the tool 100 is capable of cutting or crimping the cable 140 flush against a washer, or other component that facilitates secure coupling of the cable 140 to tissue. As used herein a tensioned cable is a tensionable cable where at least a portion of the cable is in tension.

According to some examples shown in FIGS. 1-11, 14, and 15, the tool 100 is configured to cut a tensioned cable. The tool 100 includes a handle that comprises a back handle portion 102 and a front handle portion 104 that is rotatably coupled to the back handle portion 102. The front handle portion 104 is rotatable relative to the back handle portion 102 in a rotational direction 114 to move the front handle portion 104 toward the back handle portion 102, in the direction 112, to place the tool 100 in a cable-engagement configuration. The tool 100 also include a spring element 106, coupled to and interposed between the front handle portion 104 and the back handle portion 102, that biases the front handle portion 104 away from the back handle portion 102, or biases the tool 100 into a cable-disengagement configuration. The back handle portion 102 and the front handle portion 104 can be squeezed by the hand of a user to move the tool 100 into the cable-engagement configuration from the cable-disengagement configuration.

Figure 3:
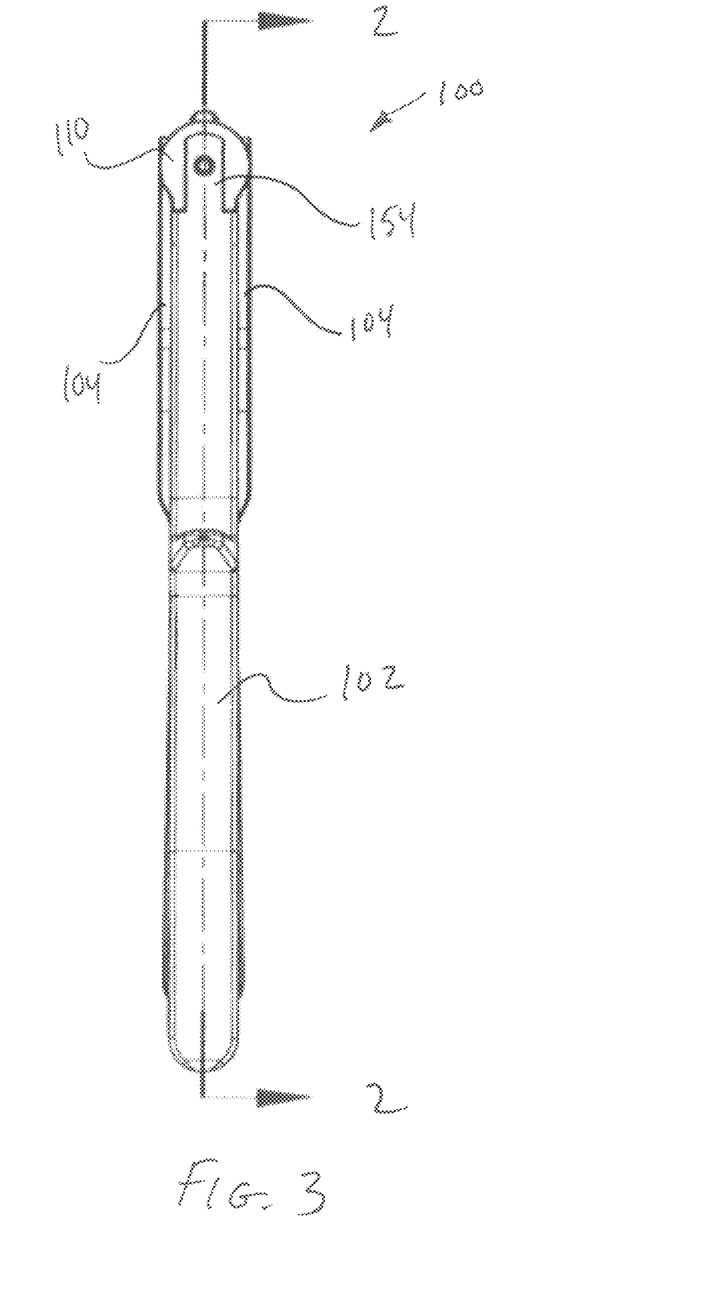
FIG. 3 is a schematic back view of the tool of FIG. 1, according to one or more examples of the present disclosure.

The tool 100 additionally includes an inner shaft 122 and an outer tube 110. The inner shaft 122 is non-movably fixed to the back handle portion 102. The outer tube 110 is movably coupled to the front handle portion 104. The outer tube 110 envelopes the inner shaft 122 (e.g., is concentric with the inner shaft 122) and is translationally movable along the inner shaft 122. Relative movement between the outer tube 110 and the inner shaft 122 is facilitated by a notch 118 formed in the outer tube 110 at a proximal end 113 of the outer tube 110 (see, e.g., FIG. 1). More specifically, a portion of the front handle portion 104 is located within the notch 118 and the notch 118 is configured such that as the front handle portion 104 moves in the direction 112, the portion of the front handle portion 104 in the notch 118 engages the notch 118 and causes the outer tube 110 to translationally move, in the direction 116, along the inner shaft 122. Referring to FIG. 3, the inner shaft 122 includes a rail 154 along which the outer tube 110 is translationally movable.

The tool 100 also includes a cable forming assembly 124 coupled to the inner shaft 122 and translationally co-movable with the inner shaft 122. Accordingly, engagement between the front handle portion 104 and the notch 118 causes the outer tube 110 to translationally move, in the direction 116, along the cable forming assembly 124. The cable forming assembly 124 includes a base shaft 126 that has a proximal end 128 and a distal end 130 opposite the proximal end 128. The proximal end 128 is directly coupled to the inner shaft 122 and is enveloped by the outer tube 110. The cable forming assembly 124 further includes a cable former 120 at and retained by the distal end 130 of the base shaft 126. A portion of the cable former 120 is not enveloped by the outer tube 110. In other words, a portion of the cable former 120 protrudes from the distal end 111 of the outer tube 110.

Figure 1:
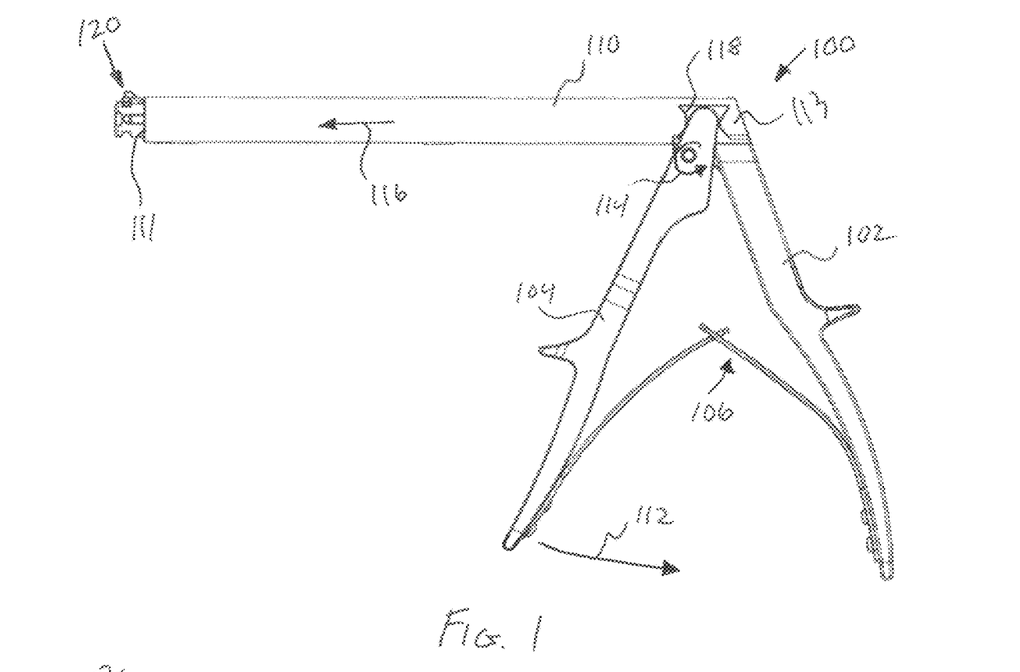
FIG. 1 is a schematic side view of a tool, according to one or more examples of the present disclosure.
Figure 2:
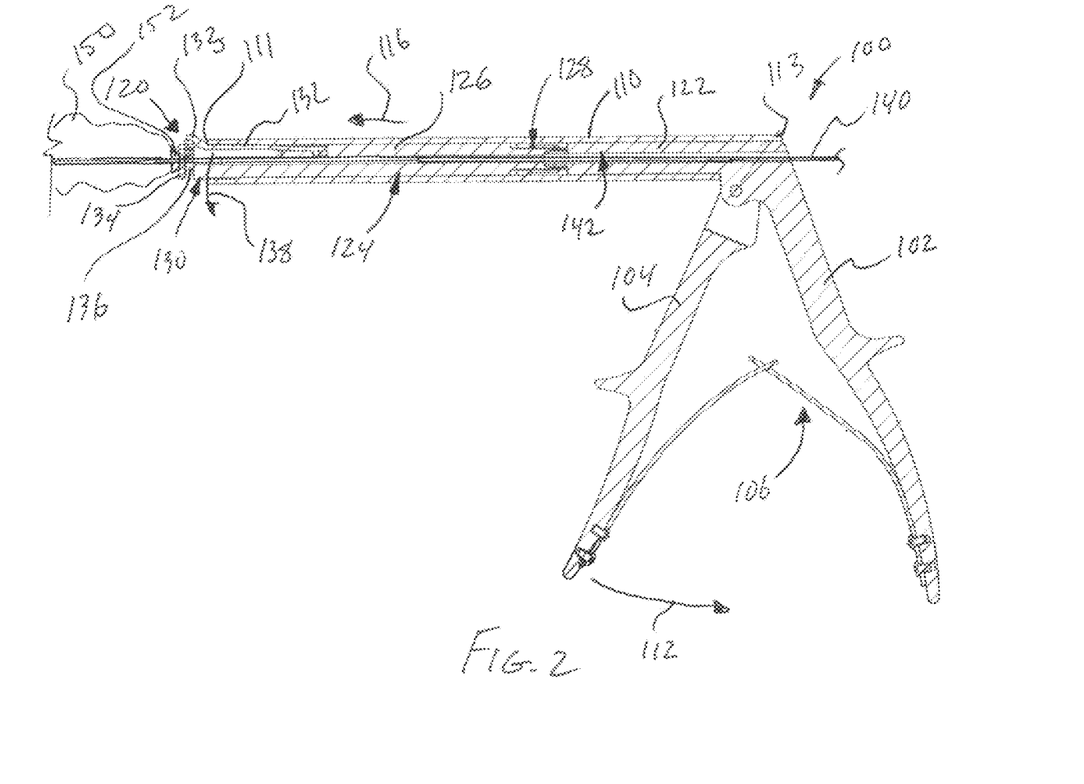
FIG. 2 is a schematic cross-sectional side view of the tool of FIG. 1, taken along the line 2-2 of FIG. 3, according to one or more examples of the present disclosure.
Figures 4, 5:
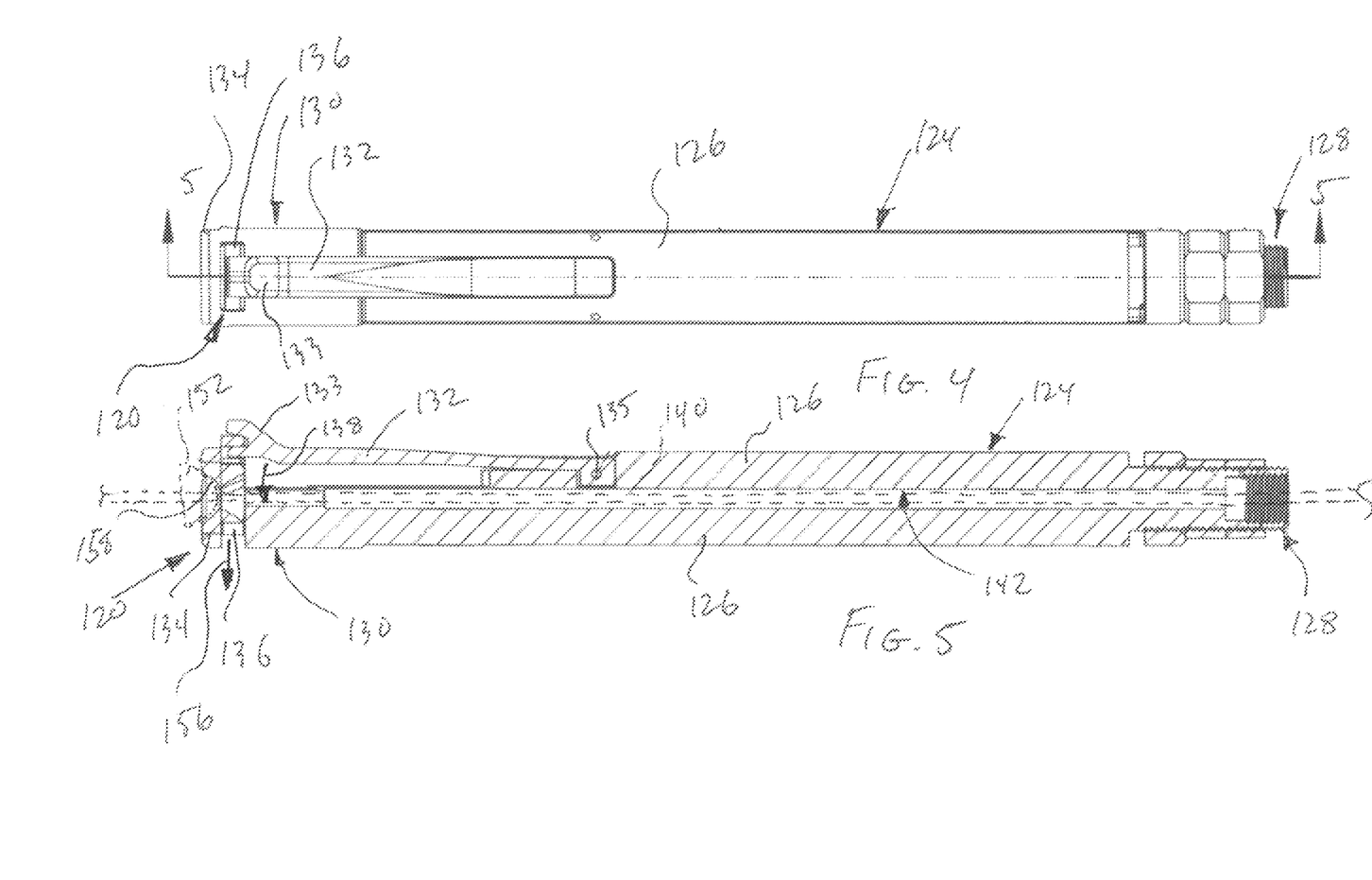
FIG. 4 is a schematic top view of a cable forming assembly of a tool, according to one or more examples of the present disclosure.
FIG. 5 is a schematic cross-sectional side view of the cable forming assembly of FIG. 4, taken along the line 5-5 of FIG. 4, according to one or more examples of the present disclosure.
Figure 7:
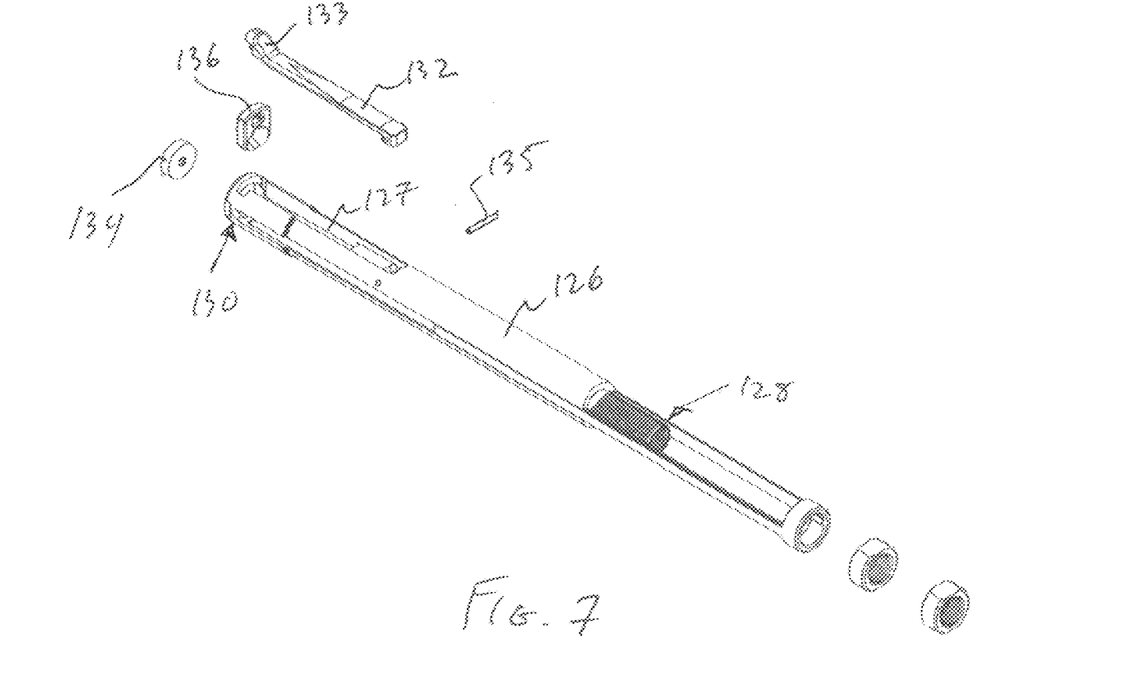
FIG. 7 is a schematic exploded perspective view of the cable forming assembly of FIG. 4, according to one or more examples of the present disclosure.
Figure 15:
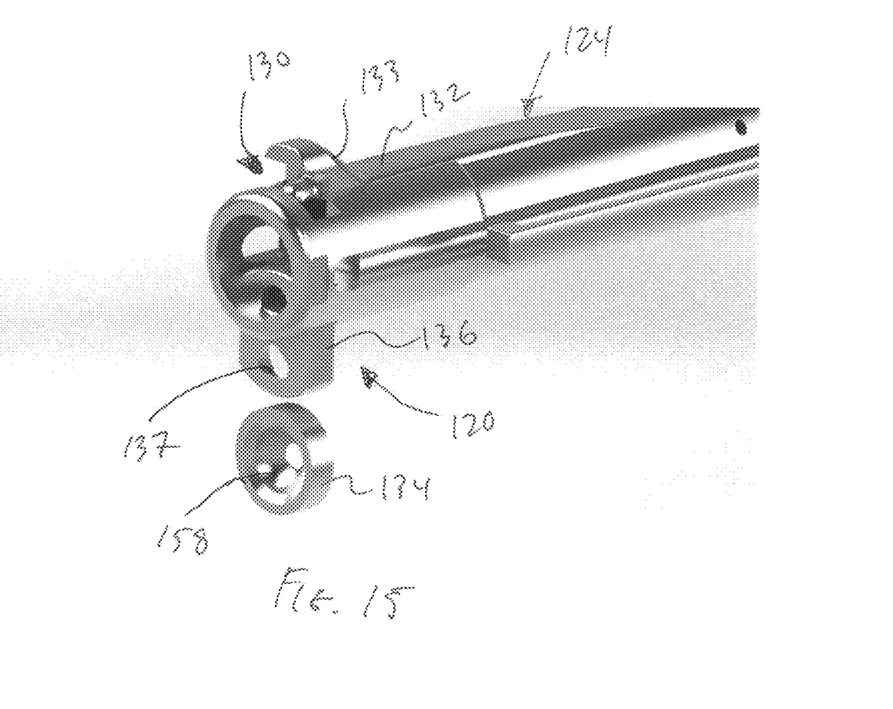
FIG. 15 is a schematic partially-exploded perspective view of a cable former of a tool, according to one or more examples of the present disclosure.

Referring to FIGS. 2, 4 and 5, the cable former 120 includes a lever 132 with an angled surface 133. The lever 132 is pivotally coupled to the base shaft 126 by a dowel pin 135, which allows the lever 132 to pivot toward the base shaft 126 in the rotational direction 138. As shown in FIG. 7, the lever 132 is positionable and pivotably movable within a slot 127 formed in the base shaft 126. The cable former 120 additionally includes a cable-forming element, which is a cutting insert 136 in the example of FIG. 7, in co-movable engagement with the lever 132. In other words, as the lever 132 rotates in the rotational direction 138, the cutting insert 136 is translationally movable in the direction 156, which is a direction angled (e.g., perpendicular) relative to the central axis of the central channel 142 or the direction 116. As shown in FIG. 15, the cutting insert 136 includes a through-aperture forming at least a portion of the central channel 142, through which a cable 140 is extendable, as explained below. At least a portion of the through-aperture includes a blade 137 having a sharp edges that is capable of cutting through the cable 140. The distal end 130 of the base shaft 126 includes a slot within which the cutting insert 136 is translationally movably retained. The cable former 120 further includes a mating insert 134 that includes a through-aperture forming at least a portion of the central channel 142, through which a cable 140 is extendable. Additionally, the mating insert 134 defines a receptacle 158. The cutting insert 136 is interposed between the mating insert 134 and distal end 111 of the outer tube 110. Moreover, the mating insert 134 abuts the cutting insert 136 such that the cutting insert 136 is slidable against the mating insert 134 as the cutting insert 136 moves in the direction 156. The receptacle 158 has a contoured shape that complements the shape of the washer 152, or other similar component, such that the washer 152 is seatable (e.g., nestably engageable) with the receptacle 158 (see, e.g., FIG. 5). In this manner, the washer 152 can be locatable approximately flush with the blade 137 of the cutting insert 136.

As shown in FIGS. 3 and 5, the tool 100 includes a central channel 142 that extends along an entire length of the tool 100, excluding the handles. In other words, the central channel 142 of the tool 100 extends entirely through the inner shaft 122, the base shaft 126, the cutting insert 136, and the mating insert 134. Defined another way, each of the inner shaft 122, the base shaft 126, the cutting insert 136, and the mating insert 134 includes a portion of the central channel 142. The central channel 142 is sized to allow the cable 140 to extend entirely therethrough as shown in FIGS. 2 and 5. Accordingly, after the cable 140 is crimped, the excess cable 140 can be threaded through the central channel 142 from the mating insert 134 to the end of the inner shaft 122. In some examples, the central channel 14.

In a cutting operation, after the cable 140 is crimped and the excess cable 140 is threaded through the central channel 142, the tool 100 is located relative to the bone 150 (or other tissue) such that the washer 152 (or other component) is seated within the receptacle 158. With the tool 100 in this position, a user squeezes the back handle portion 102 and the front handle portion 104 together to translationally move the outer tube 110, in the direction 116, until the distal end 111 of the outer tube 110 contacts the angled surface 133. Further squeezing together of the back handle portion 102 and the front handle portion 104 forces the distal end 11 to slide along the angled surface 133, which causes the lever 132 to pivot in the rotational direction 138 and urge the cutting insert 136 in the direction 156. With the cable 140 passing through the central channel 142, the blade 137 cuts through the cable 140 as the cutting insert 136 moves in the direction 156. Moreover, because the washer 152 is located approximately flush with the blade 137 of the cutting insert 136, the cable 140 is cut approximately flush with the washer 152. Accordingly, excess cable 140 extending from the washer 142 after the cable 140 is cut, which would require extra operational steps to remove, is virtually eliminated.

Figure 6:
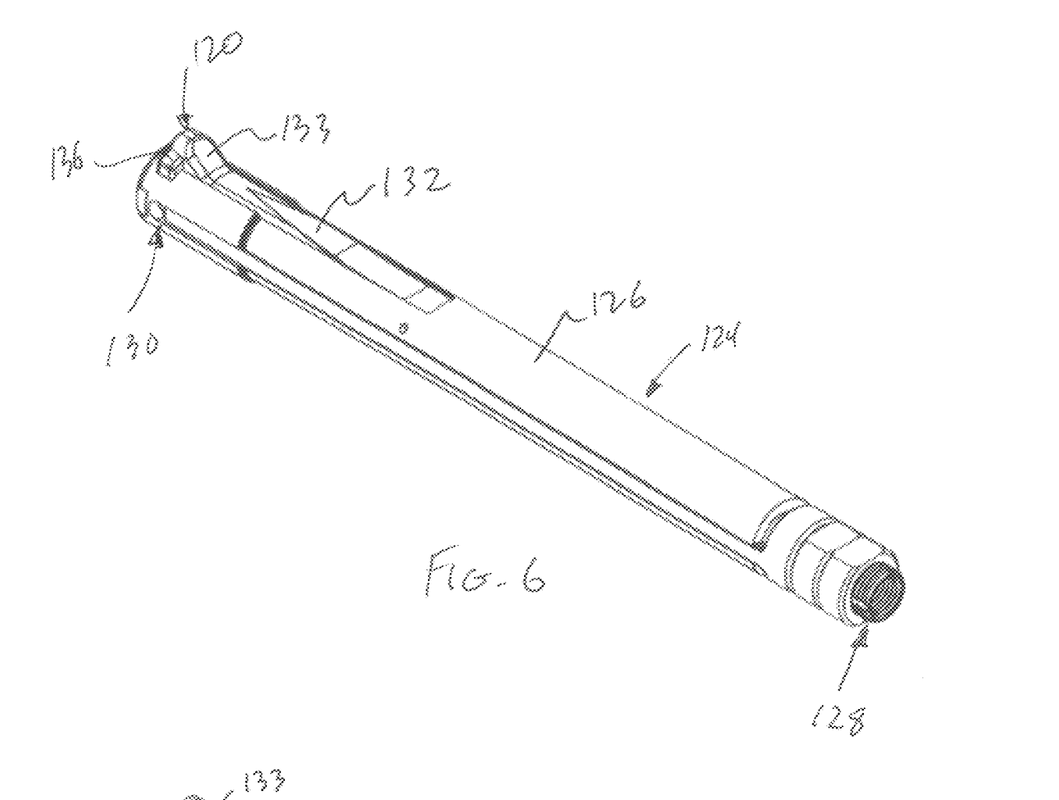
FIG. 6 is a schematic perspective view of the cable forming assembly of FIG. 4, according to one or more examples of the present disclosure.

Referring to FIGS. 6 and 7, in some examples, an overall length of the cable forming assembly 124 is adjustable to accommodate cutting of differently sized cables or adjust the range of motion of the handles necessary to cut the cable 140.

Figure 12:
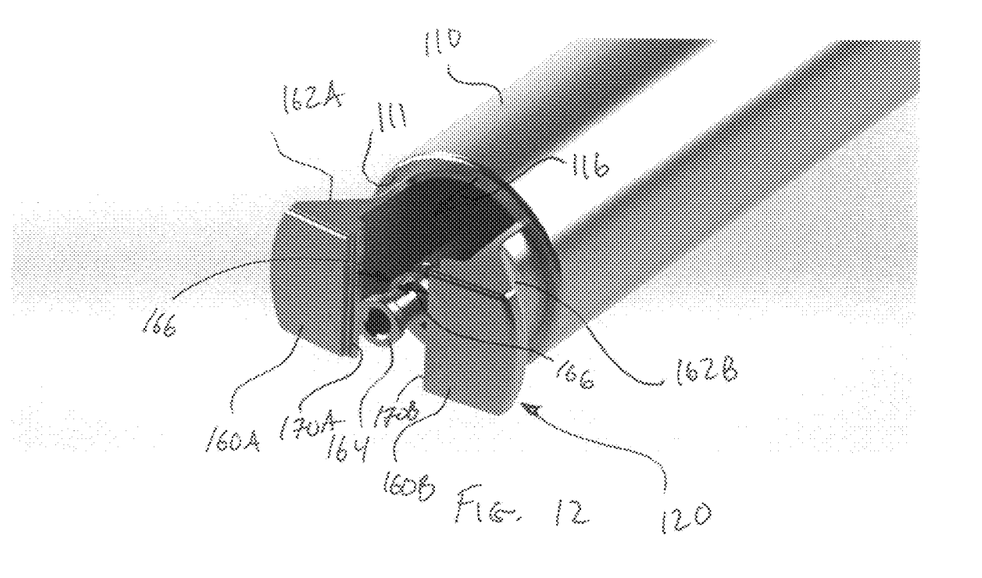
FIG. 12 is a schematic perspective view of a cable former of a tool and a crimping element, according to one or more examples of the present disclosure.
Figure 13:
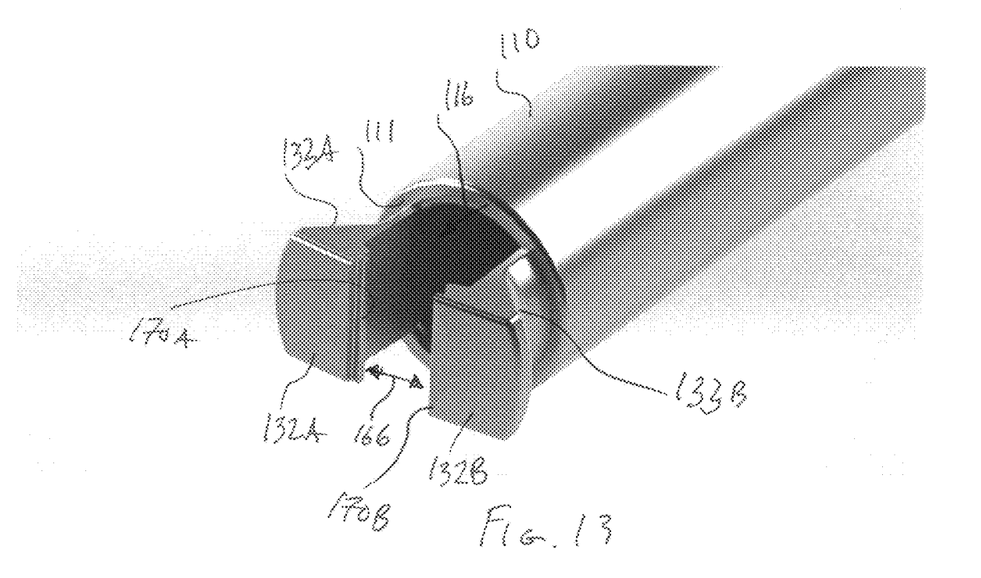
FIG. 13 is a schematic perspective view of a cable former of a tool, according to one or more examples of the present disclosure.
Figure 14:
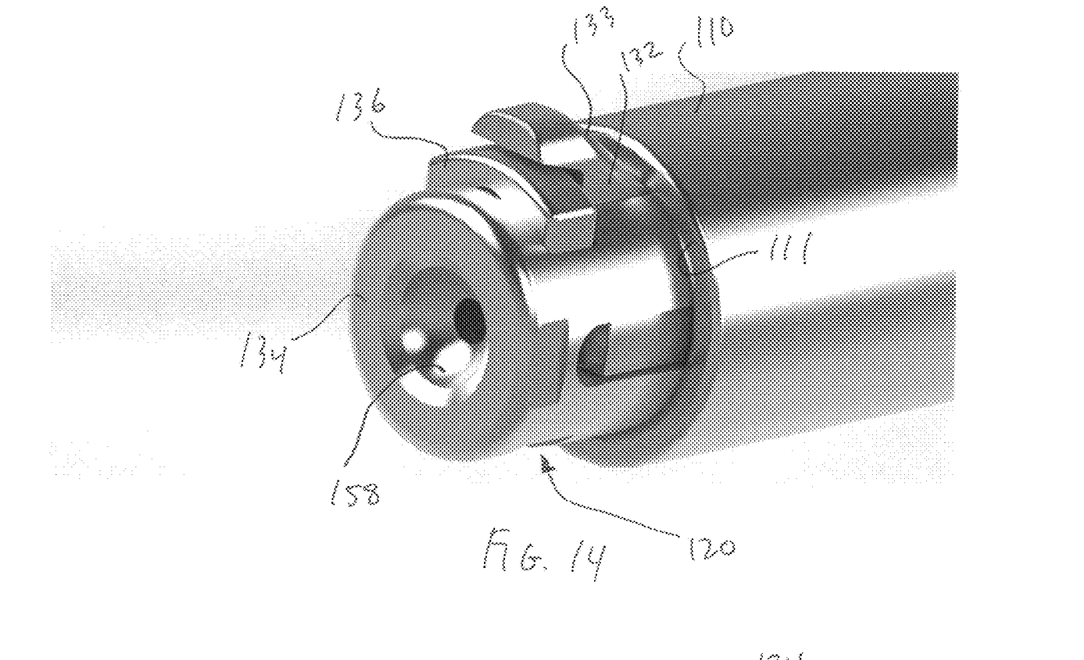
FIG. 14 is a schematic perspective view of a cable former of a tool, according to one or more examples of the present disclosure.

Now referring to FIGS. 12 and 13, in alternative examples, the tool 100 is configured to crimp a tensioned cable. Accordingly, instead of the cable-forming element being a cutting insert 136, engageable with a mating insert 134, the cable-forming element of the cable former 120, as shown in FIGS. 12 and 13, includes a first crimping die 170A and a second crimping die 170B that cooperatively crimp a cable. More specifically, the first crimping die 170A and the second crimping die 170B oppose each other and are movable toward each other, in the direction 166, to crimp a cable between the first crimping die 170A and the second crimping die 170B. The first crimping die 170A forms part of a first lever 132A of the cable former 120 (e.g., forms a one-piece monolithic unit with the first lever 132A) and the second crimping die 170B forms part of a second lever 132B of the cable former 120 (e.g., forms a one-piece monolithic unit with the second lever 132B). In other words, instead of a single lever, such as with the tool 100 of FIGS. 1-11, 14, and 15, the cable former 120 of the tool 100 of FIGS. 12 and 13 includes two, opposing, levers. Each of the first lever 132A and the second lever 132B includes a corresponding one of a first angled surface 133A and a second angled surface 133B. Like the lever 132 and the angled surface 133, as the distal end 111 of the outer tube 110 is moved in the direction 116 along the first angled surface 133A and the second angled surface 133B, the outer tube 110 forces the first lever 132A and the second lever 132B toward each other in the direction 166. Therefore, when a cable is between the first crimping die 170A and the second crimping die 170B, squeezing the handles of the tool together causes the first crimping die 170A and the second crimping die 170B to compress, deform, and crimp the cable.

As shown in FIG. 12, a crimping element 164 (e.g., a washer) can be located around the cable and between the first crimping die 170A and the second crimping die 170B. When the tool 100 is actuated to bring the first crimping die 170A and the second crimping die 170B together, the crimping element 164 is deformed against the cable to crimp the cable.

The cable forming assembly 124 is selectively releasably coupled to the inner shaft 122, via any of various types of releasably couplings, such as threaded engagement. Accordingly, in some examples, one cable forming assembly 124 can be interchangeable with another cable forming assembly 124. In this manner, a single tool 100 can performed multiple functions by replacing one cable forming assembly 124 that performs a first operation (e.g., cutting) with another cable forming assembly 124 that performs a second operation (e.g., crimping) different than the first operation.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope.

What is claimed is:

1. A tool for cutting cable in a medical procedure, the tool comprising:
   an inner shaft;
   an outer tube within which the inner shaft is positioned, wherein the outer tube is concentric with the inner shaft and translationally movable along the inner shaft;
   a cable forming assembly coupled with the inner shaft such that the cable forming assembly is co-movable with the inner shaft and the outer tube is translationally movable along the cable forming assembly, wherein the cable forming assembly comprises:
      a lever pivotable relative to the outer tube and positioned to engage the outer tube as the outer tube translationally moves along the inner shaft in an engagement direction; and
      a cutting insert translationally movable in a cutting direction and engaged with the lever;
   a central channel, which extends through the inner shaft, the outer tube, and the cable forming assembly along an entire length of each one of the inner shaft, the outer tube, and the cable forming assembly;
   wherein:
      the cutting insert comprises a circumferentially-closed through-aperture that defines a portion of the central channel;
      the cutting insert is actuatable to cut the cable when the cable passes through the circumferentially-closed through-aperture of the cutting insert;
      translational movement of the outer tube along the inner shaft in the engagement direction pivots the lever in a rotational direction, relative to the outer tube, and translationally moves the cutting insert in the cutting direction to cut the cable; and
      the cutting direction is angled relative to the engagement direction.

2. The tool according to claim 1, further comprising a handle coupled to the inner shaft and the outer shaft, wherein the handle is manually operable to translationally move the outer shaft along the inner shaft in the engagement direction.

3. The tool according to claim 2, wherein:
   the handle comprises a back handle portion non-movably fixed to the inner shaft;
   the handle further comprises a front handle portion movably coupled to the outer tube; and
   manual movement of the front handle portion towards the back handle portion urges the outer shaft to translationally move along the inner shaft in the engagement direction.

4. The tool according to claim 1, wherein:
   the lever comprises an angled surface, which is angled relative to the engagement direction; and
   engagement between the outer tube and the lever comprises the outer tube sliding along the angled surface.

5. The tool according to claim 1, wherein:
   the cutting insert further comprises a blade formed in at least a portion of the circumferentially-closed through-aperture; and
   the blade is configured to cut the cable when the cable passes through the circumferentially-closed through-aperture of the cutting insert and when the cutting insert is moved in the cutting direction.

6. The tool according to claim 5, wherein:
   the cable forming assembly further comprises a mating insert, which comprises a second circumferentially-closed through-aperture that defines a portion of the central channel;
   the mating insert further comprises a receptacle, which has a contoured shape; and
   the mating insert defines a distal-most surface of the tool.

7. The tool according to claim 6, wherein the mating insert abuts the cutting insert such that the cutting insert is slidable against the mating insert as the cutting insert moves in the cutting direction.

8. The tool according to claim 6, wherein a distal-most surface of the cutting insert abuts a proximal-most surface of the mating insert.

9. The tool according to claim 8, wherein the blade is approximately flush with the proximal-most surface of the mating insert.

10. The tool according to claim 5, wherein the blade is curved.

11. The tool according to claim 1, wherein the cutting direction is perpendicular to the engagement direction.

12. The tool according to claim 1, wherein:
the cable forming assembly further comprises a base shaft positioned within the outer tube and concentric with the inner shaft;
the base shaft comprises a proximal end coupled directly to the inner shaft such that the base shaft is co-movably fixed to the inner shaft;
the base shaft comprises a distal end, which is opposite the proximal end; and
the outer tube is translationally movable along the base shaft.

13. The tool according to claim 12, wherein the distal end of the base shaft is selectively releasably coupled to the inner shaft.

14. The tool according to claim 13, wherein:
the tool further comprises a plurality of cable forming assemblies;
each one of the plurality of cable forming assemblies is selectively interchangeably coupleable with the distal end of the base shaft; and
each one of the plurality of cable forming assemblies is configured differently than any other one of the plurality of cable forming assemblies.

15. The tool according to claim 1, wherein the circumferentially-closed through-aperture converges in the engagement direction.

16. The tool according to claim 1, wherein the circumferentially-closed through-aperture has a cone shape.

17. A system for cutting a cable in a medical procedure, the system comprising:
a tensionable cable;
a washer, configured to retain the tensionable cable;
a tool, comprising:
an inner shaft;
an outer tube within which the inner shaft is positioned, wherein the outer tube is concentric with the inner shaft and translationally movable along the inner shaft;
a cable forming assembly coupled with the inner shaft such that the cable forming assembly is co-movable with the inner shaft and the outer tube is translationally movable along the cable forming assembly, wherein the cable forming assembly comprises:
a lever pivotable relative to the outer tube and positioned to engage the outer tube as the outer tube translationally moves along the inner shaft in an engagement direction; and
a cutting insert translationally movable in a cutting direction and engaged with the lever;
a central channel, which extends through the inner shaft, the outer tube, and the cable forming assembly along an entire length of each one of the inner shaft, the outer tube, and the cable forming assembly;
wherein:
the cable forming assembly further comprises
a mating insert, which comprises a second circumferentially-closed through-aperture that defines a portion of the central channel;
the cutting insert comprises a circumferentially-closed through-aperture that defines a portion of the central channel;
the cutting insert is actuatable to cut the cable when the cable passes through the circumferentially-closed through-aperture of the cutting insert;
translational movement of the outer tube along the inner shaft in the engagement direction pivots the lever in a rotational direction, relative to the outer tube, and translationally moves the cutting insert in the cutting direction to cut the cable;
the mating insert further comprises a receptacle, which has a contoured shape that complements a shape of the washer such that the washer is seatably engaged with the receptacle when the cutting insert cuts the cable; and
the cutting direction is angled relative to the engagement direction.

* * * * *